United States Patent
Gras et al.

(10) Patent No.: US 9,689,859 B2
(45) Date of Patent: Jun. 27, 2017

(54) ANALYTICAL METHOD FOR DETECTING FUEL MARKERS

(71) Applicants: Dow Global Technologies LLC, Midland, MI (US); Rohm and Haas Company, Philadelphia, PA (US)

(72) Inventors: Ronda L. Gras, Edmonton (CA); Jim C. Luong, Sherwood Park (CA); Warren E. Smith, Buckinghamshire (GB)

(73) Assignees: Dow Global Technologies LLC, Midland, MI (US); Rohm and Haas Company, Philadelphia, PA (US)

( * ) Notice: Subject to any disclaimer, the term of this patent is extended or adjusted under 35 U.S.C. 154(b) by 11 days.

(21) Appl. No.: 14/787,521

(22) PCT Filed: May 2, 2014

(86) PCT No.: PCT/US2014/036493
§ 371 (c)(1),
(2) Date: Oct. 28, 2015

(87) PCT Pub. No.: WO2014/179647
PCT Pub. Date: Nov. 6, 2014

(65) Prior Publication Data
US 2016/0178602 A1  Jun. 23, 2016

Related U.S. Application Data

(60) Provisional application No. 61/818,509, filed on May 2, 2013.

(51) Int. Cl.
| | |
|---|---|
| G01N 30/28 | (2006.01) |
| G01N 33/28 | (2006.01) |
| C10L 1/00 | (2006.01) |
| G01N 30/46 | (2006.01) |
| G01N 30/88 | (2006.01) |
| G01N 30/04 | (2006.01) |

(52) U.S. Cl.
CPC .......... G01N 33/2882 (2013.01); C10L 1/003 (2013.01); G01N 30/468 (2013.01); *G01N 2030/047* (2013.01); *G01N 2030/8854* (2013.01)

(58) Field of Classification Search
CPC ............. G01N 33/2882; G01N 30/468; G01N 2030/047; G01N 2030/8854; C10L 1/003
See application file for complete search history.

(56) References Cited

U.S. PATENT DOCUMENTS

| | | | |
|---|---|---|---|
| 5,474,937 A * | 12/1995 | Anderson, II | ........ C06B 23/008 436/139 |
| 5,492,555 A | 2/1996 | Strunk et al. | |
| 5,981,283 A | 11/1999 | Anderson, II et al. | |
| 7,858,373 B2 | 12/2010 | Banavali et al. | |
| 8,322,189 B2 | 12/2012 | Wang | |
| 9,222,928 B2 * | 12/2015 | Green | ..................... C10L 1/003 |
| 2003/0087454 A1 | 5/2003 | Schultz et al. | |
| 2003/0096419 A1 | 5/2003 | Trigiani | |
| 2004/0248307 A1 | 12/2004 | Grof et al. | |
| 2009/0100906 A1 | 4/2009 | Bonne | |
| 2009/0218286 A1 | 9/2009 | Bisschops et al. | |
| 2014/0075829 A1 | 3/2014 | Green et al. | |
| 2014/0134746 A1 | 5/2014 | Green et al. | |

FOREIGN PATENT DOCUMENTS

DE    1130204 B    5/1962

OTHER PUBLICATIONS

Seeley, "Recent advances in flow-controlled multidimensional gas chromatography", J. Chrom. A, pp. 1-14 (2012).
Sasamoto, et al., "Selectable one-dimensional or two-dimensional gas chromatography-mass spectrometry with simultaneous olfactometry or element-specific detection", J. Chrom. A., vol. 1217 pp. 2903-2910 (2010).
Tranchida, et al., "Heart-cutting multidimensional gas chromatography: A review of recent evolution, applications, and future propspects", Analytica Chimica Acts, vol. 716, pp. 66-75 (2012).

\* cited by examiner

*Primary Examiner* — David Z Huang
(74) *Attorney, Agent, or Firm* — Kenneth Crimaldi

(57) ABSTRACT

A gas chromatographic method for detecting a first marker and a second marker in a fuel in two channels: (i) a first capillary column coated with polysiloxane and a second capillary column coated with polyethylene glycol; and (ii) a third capillary column coated with polymethylphenylsiloxane and a fourth deactivated capillary column. The steps are: (a) introducing a first sample into the first column to produce a first effluent; (b) introducing only a portion of the first effluent into the second column to produce a second effluent; (c) allowing the second effluent to pass through a mass spectrometer; (d) introducing a second sample into the third column to produce a third effluent; (e) introducing only a portion of the third effluent into the fourth column to produce a fourth effluent; (f) allowing the fourth effluent to pass through a mass spectrometer.

7 Claims, No Drawings

ANALYTICAL METHOD FOR DETECTING FUEL MARKERS

This invention relates to an analytical method useful in detecting two marker compounds in a complex liquid hydrocarbon matrix.

Marking of petroleum hydrocarbons and other fuels and oils with various kinds of chemical markers is well known in the art. A variety of compounds have been used for this purpose, as well as numerous techniques for detection of the markers, e.g., absorption spectroscopy and mass spectrometry. For example, U.S. Pat. No. 7,858,373 discloses the use of a variety of organic compounds for use in marking liquid hydrocarbons and other fuels and oils. Combinations of markers can be used as digital marking systems, with the ratios of amounts forming a code for the marked product. Some marker compounds for these products are difficult to detect in the marked fuel by chromatographic separation. The problem addressed by this invention is to find a method for detecting two marker compounds in a complex liquid hydrocarbon matrix.

STATEMENT OF INVENTION

The present invention provides a gas chromatographic method for detecting a first marker compound and a second marker compound in a petroleum hydrocarbon or a liquid biologically derived fuel; said method comprising providing two analysis channels, (i) and (ii); wherein channel (i) comprises a first capillary column which is an open tubular column coated with a polysiloxane stationary phase and a second capillary column which is an open tubular column coated with a polyethylene glycol; and channel (ii) comprises a third capillary column which is an open tubular column coated with a polymethylphenylsiloxane having at least 30 mole % phenyl substitution and a fourth capillary column which is a deactivated open tubular column; and said method comprising steps of: (a) determining retention times of the first marker compound in the first and second capillary columns and the second marker compound in the third and fourth capillary columns; (b) introducing a first sample of a petroleum hydrocarbon or a liquid biologically derived fuel into the first channel and allowing the first sample to flow through the first capillary column to produce a first effluent stream; (c) introducing only a portion of the first effluent stream having a retention time range which includes the retention time of the first marker compound into the second capillary column and allowing said portion of the first effluent stream to flow through the second capillary column to produce a second effluent stream; (d) allowing the second effluent stream to pass through a mass spectrometer; (e) introducing a second sample of a petroleum hydrocarbon or a liquid biologically derived fuel into the second channel and allowing the sample to flow through the third capillary column to produce a third effluent stream; (f) introducing only a portion of the third effluent stream having a retention time range which includes the retention time of the second marker compound into the fourth capillary column and allowing said portion of the third effluent stream to flow through the fourth capillary column to produce a fourth effluent stream; and (g) allowing the fourth effluent stream to pass through a mass spectrometer;

wherein the first marker compound has formula $Ar^1(R^2)_m(OR^1)_n$, wherein $Ar^1$ is an aromatic ring system having from six to twenty carbon atoms, $R^1$ is $C_1$-$C_{12}$ alkyl or $C_2$-$C_{12}$ alkenyl, $R^2$ is $C_1$-$C_{12}$ alkyl or $C_3$-$C_{12}$ alkenyl, m is an integer from zero to five and n is an integer from one to three; the second marker compound has three or four unfused benzene rings, a total of 20 to 60 carbon atoms and at least one alkyl or alkoxy substituent having one to eighteen carbon atoms; and wherein each marker compound is present in the petroleum hydrocarbon or a liquid biologically derived fuel at a level from 0.01 ppm to 100 ppm.

DETAILED DESCRIPTION

Percentages are weight percentages (wt %) and temperatures are in ° C., unless specified otherwise. Boiling points mentioned herein are measured at atmospheric pressure. Concentrations are expressed either in parts per million ("ppm") calculated on a weight/weight basis, or on a weight/volume basis (mg/L); preferably on a weight/volume basis. The term "petroleum hydrocarbon" refers to products having a predominantly hydrocarbon composition, although they may contain minor amounts of oxygen, nitrogen, sulfur or phosphorus; petroleum hydrocarbons include crude oils as well as products derived from petroleum refining processes; they include, for example, crude oil, lubricating oil, hydraulic fluid, brake fluid, gasoline, diesel fuel, kerosene, jet fuel and heating oil. Marker compounds of this invention can be added to a petroleum hydrocarbon or a liquid biologically derived fuel; examples of the latter are biodiesel fuel, ethanol, butanol, ethyl tert-butyl ether or mixtures thereof. A substance is considered a liquid if it is in the liquid state at 20° C. A biodiesel fuel is a biologically derived fuel containing a mixture of fatty acid alkyl esters, especially methyl esters. Biodiesel fuel typically is produced by transesterification of either virgin or recycled vegetable oils, although animal fats may also be used. An ethanol fuel is any fuel containing ethanol, in pure form, or mixed with petroleum hydrocarbons, e.g., "gasohol." An "alkyl" group is a substituted or unsubstituted saturated hydrocarbyl group having from one to twenty-two carbon atoms in a linear, branched or cyclic arrangement. Substitution on alkyl groups of one or more OH or alkoxy groups is permitted; other groups may be permitted when specified elsewhere herein. Preferably, alkyl groups are unsubstituted. Preferably, alkyl groups are linear or branched. An "alkenyl" group is an alkyl group having at least one carbon-carbon double bond. Preferably, alkenyl groups have one or two carbon-carbon double bonds, preferably one. An "aryl" group is a substituent derived from an aromatic hydrocarbon compound. An aryl group has a total of from six to twenty ring atoms, unless otherwise specified, and has one or more rings which are separate or fused. Preferably, the marker compounds contain elements in their naturally occurring isotopic proportions.

A "capillary column" is a column suitable for gas chromatography having an inner diameter from 75 to 750 µm, preferably from 100 to 550 µm, preferably from 150 to 400 µm, preferably from 150 to 350 µm and a length of 5 to 100 m, preferably 7 to 60 m. Preferably, when a mass spectrometer is used as a detector the column diameter is no greater than 400 µm, preferably no greater than 350 µm, preferably no greater than 330 µm. Preferably, capillary columns are made from polyimide-coated fused silica glass or passivated metal. A deactivated column is a glass column which has been treated to neutralize active silanol groups and remove impurities on the glass surface, preferably by alkaline etching (stripping) or chemical vapor deposition. In the present method, the columns are in one or more ovens of the type usually used in gas chromatographs, and the injectors are of the typical configuration; samples are introduced into the columns in an inert carrier gas. Preferably, the amount of sample injected into the gas chromatograph is from 0.2 to 5

µL, preferably from 0.5 to 3 µL, preferably from 0.8 to 2 µL. Preferably the sample is undiluted petroleum hydrocarbon or liquid biologically derived fuel. Preferably the injection is split such that the ratio of total injection to the amount sent to the first (or third) column is from 25:1 to 15:1, preferably about 20:1. For the first channel, with columns 1 and 2, preferably, the oven temperature for the columns initially is from 25 to 200° C., preferably from 40 to 150° C., preferably from 50 to 100° C. and then increases to a temperature from 180 to 350° C., preferably from 200 to 325° C., preferably from 200 to 250° C. For the second channel, with columns 3 and 4, preferably, the oven temperature for the columns initially is from 25 to 200° C., preferably from 40 to 150° C., preferably from 50 to 100° C. and then increases to a temperature from 300 to 450° C., preferably from 325 to 425° C., preferably from 350 to 400° C. Preferably, the first and second columns are in a first oven and the third and fourth columns are in a second oven. Preferably, the carrier gas (preferably helium) flow rate is from 0.2 to 30 mL/min, preferably from 0.5 to 20 mL/min, preferably from 1 to 10 mL/min. Those skilled in the art will appreciate that the parameters mentioned above are interrelated and are not critical individually, but they can be adjusted together to achieve optimum separation of the desired compounds.

A "polysiloxane" stationary phase is one which is based on polydimethylsiloxane. Preferably, the polysiloxane stationary phase is an unsubstituted polydimethylsiloxane or a polydimethylsiloxane substituted with phenyl, cyanopropyl or trifluoromethyl groups; preferably phenyl or cyanopropyl (no greater than 30 mole % substitution of these groups for methyl, preferably no more than 25 mole %, preferably no more than 20 mole %); or a polydimethylsiloxane with embedded aryl groups, preferably phenylene groups (no more than 30 mole %). Preferably, the polyethylene glycol has a number average molecular weight from 10,000 to 30,000, preferably from 15,000 to 25,000. An especially preferred polyethylene glycol is CARBOWAX 20M. Preferably, when a mass spectrometer is used as a detector, the second column is a polyethylene glycol column. A "polymethylphenylsiloxane having more than 30 mole % phenyl substitution" is a polydimethylsiloxane in which at least 30 mole % of the methyl groups has been replaced with phenyl groups, preferably at least 40 mole %, preferably at least 50 mole %.

The effluents from the second and fourth capillary columns pass through a mass spectrometer. The retention-time range in which each marker elutes from each column is determined previously by injection of the markers themselves under the same conditions used for the subsequent steps in the method. Other detectors may be used in addition to the mass spectrometer by using splitters to divert effluents to more than one detector. Other suitable detectors include flame ionization detectors (FID), atomic emission detectors, pulsed discharge helium ionization detectors, dielectric barrier detectors, thermal conductivity detectors and helium ionization detectors. In a preferred embodiment of the invention, the effluent from the second channel is sent to both a mass spectrometer and an FID; in this embodiment preferably a fifth column which is substantially identical to the fourth column is used to carry effluent to the FID, while effluent from the fourth column goes to the mass spectrometer. Typically, the first marker elutes from the nonpolar column at a retention time that would place it under the peaks due to components of the petroleum hydrocarbon or liquid biologically derived fuel where it cannot be detected, while the second marker elutes at a retention time longer than those of most of the fuel components. Preferably the retention time ranges are wide enough to ensure that each marker (if present) would elute in the target range but narrow enough to avoid sending most of the petroleum hydrocarbon or a liquid biologically derived fuel to the second column. The retention times will vary greatly depending on the conditions, but can easily be determined for each marker and set of conditions. Any standard switching device suitable for use in gas chromatography can be used to divert the portion of any effluent which is not to be introduced into another column. Preferably a pneumatically activated rotary or slider valve or a non-contact switching valve, preferably a Deans switch is used. Preferably, the portion of any effluent that is not to be sent to another capillary column is diverted to waste. Preferably, the injections into the first and second channels are coordinated so that the second and fourth effluent streams may be sent to a single mass spectrometer without overlapping. Preferably, only a single mass spectrometer is connected to the first and second channels. Preferably, in the first channel, the first column is back-flushed after the portion of the first effluent containing the first marker has eluted; this is accomplished either pneumatically or with a rotary valve. The flushed material exits the system through the split vent. Preferably, in the second channel, most of the third effluent is vented and not transferred to the fourth column, preferably at least 60 wt % is vented, preferably at least 70 wt %, preferably at least 80 wt %, preferably at least 85 wt %.

For the first marker, preferably, $R^1$ is linear or branched. Preferably, $R^2$ is linear or branched. Preferably, $R^1$ is $C_4$-$C_{12}$ alkyl or $C_4$-$C_{12}$ alkenyl, preferably $C_4$-$C_{12}$ alkyl, preferably $C_4$-$C_{10}$ alkyl. Preferably, $R^2$ is $C_1$-$C_6$ alkyl or $C_3$-$C_6$ alkenyl, preferably $C_1$-$C_6$ alkyl, preferably $C_1$-$C_4$ alkyl, preferably methyl or ethyl. Preferably, n is one or two, preferably one. Preferably, m is from zero to two, preferably zero or one, preferably zero. Preferably, $Ar^1$ represents a benzene ring system and the compound of formula $Ar^1(R^2)_m(OR^1)_n$ is described by formula (I)

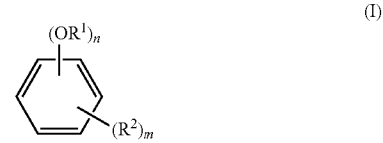

(I)

Preferably, in formula (I), $R^1$ is $C_4$-$C_{12}$ alkyl or $C_4$-$C_{12}$ alkenyl, preferably $C_4$-$C_{12}$ alkyl, preferably $C_4$-$C_{10}$ alkyl; preferably $R^2$ is $C_1$-$C_6$ alkyl or $C_3$-$C_6$ alkenyl, preferably $C_1$-$C_6$ alkyl, preferably $C_1$-$C_4$ alkyl, preferably methyl or ethyl. Preferably, in formula (I), m is from zero to two, preferably zero or one, preferably zero; preferably, n is one or two, preferably one. In one preferred embodiment, in formula (I), n is two or three, $R^1$ is methyl, $R^2$ is methyl or is absent (m=0) and m is zero or one; preferably n is two or three, $R^1$ is methyl and m is zero.

In one preferred embodiment, the compound of formula $Ar^1(R^2)_m(OR^1)_n$ is described by formula (II)

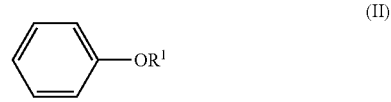

(II)

in which $R^1$ is $C_4$-$C_{12}$ alkyl or $C_4$-$C_{12}$ alkenyl, preferably $C_4$-$C_{12}$ alkyl, preferably $C_4$-$C_{10}$ alkyl.

In one preferred embodiment, $Ar^1$ has from 10 to 12 carbon atoms, n is one or two, $R^1$ is methyl, $R^2$ is methyl or is absent (m=0) and m is zero or one; preferably Ar is a substituted (substituted only by —$OR^1$) biphenyl or naphthalene, n is one or two, $R^1$ is methyl and m is zero.

The second marker compound preferably has 22 to 55 carbon atoms, preferably 25 to 50. Preferably there are at least two substituents chosen from alkyl and alkoxy; preferably each substituent has from one to twelve carbon atoms. Preferably, the second marker compound has formula $(Ph_3C)_k Ar^2 (R^3 VOR^4)_i$, wherein Ph represents a phenyl group, $Ar^2$ is an aromatic ring system having from six to twenty carbon atoms, $R^3$ and $R^4$ independently are $C_1$-$C_{18}$ alkyl, $C_3$-$C_{18}$ alkenyl or $C_4$-$C_{18}$ heteroalkyl, k is one or two, j is an integer from one to four and i is an integer from one to three.

$Ar^2$ is an aromatic ring system having from six to twenty carbon atoms and whose substituents include $Ph_3C$, $R^3$ and $OR^4$ groups, preferably one in which the only substituents are $Ph_3C$, $R^3$ and $OR^4$ groups. Preferably, $Ar^2$ is a $C_6$-$C_{12}$ hydrocarbyl aromatic ring system. Preferably, $Ar^2$ is benzene, naphthalene, biphenyl, phenyl ether, diphenylmethane or one of the preceding systems substituted with alkyl and/or alkoxy groups; preferably benzene. Preferably, i is one or two, preferably one. Preferably, k is one. Preferably, j is from one to three, preferably one or two. Preferably, $R^3$ is $C_2$-$C_{12}$ alkyl, $C_3$-$C_{12}$ alkenyl or $C_4$-$C_{12}$ heteroalkyl; preferably $C_2$-$C_{12}$ alkyl, preferably $C_3$-$C_8$ alkyl or $C_4$-$C_8$ heteroalkyl, preferably $C_2$-$C_8$ alkyl, preferably $C_3$-$C_8$ alkyl, preferably $C_3$-$C_6$ alkyl, preferably $C_2$-$C_6$ alkyl, preferably $C_2$-$C_5$ alkyl, preferably sec-butyl, t-butyl or isopropyl. Preferably, $R^3$ is saturated. Preferably, $R^3$ is linear or branched. Preferably, $R^4$ is $C_2$-$C_{18}$ alkyl, $C_3$-$C_{18}$ alkenyl or $C_4$-$C_{18}$ heteroalkyl; preferably $C_4$-$C_{18}$ alkyl, $C_4$-$C_{18}$ alkenyl or $C_4$-$C_{18}$ heteroalkyl; preferably $C_2$-$C_{18}$ alkyl, preferably $C_3$-$C_{18}$ alkyl or $C_4$-$C_{12}$ heteroalkyl, preferably $C_3$-$C_{18}$ alkyl, preferably $C_4$-$C_{18}$ alkyl, preferably $C_6$-$C_{18}$ alkyl, preferably $C_6$-$C_{16}$ alkyl, preferably $C_{10}$-$C_{14}$ alkyl. Preferably, $R^4$ is saturated. Preferably, $R^4$ is linear or branched, preferably branched.

Preferably, the second marker has formula (III)

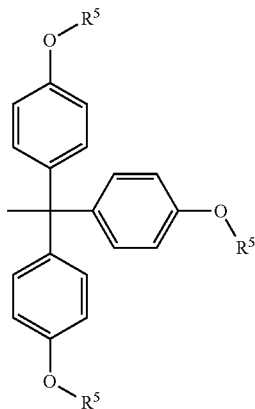

(III)

wherein $R^5$ is $C_1$-$C_{12}$ alkyl, $C_3$-$C_{12}$ alkenyl or $C_7$-$C_{12}$ aralkyl. Preferably R is $C_1$-$C_{10}$ alkyl, $C_3$-$C_{12}$ alkenyl or $C_7$-$C_{12}$ aralkyl; preferably $C_2$-$C_{10}$ alkyl, $C_3$-$C_{10}$ alkenyl or $C_7$-$C_{12}$ aralkyl; preferably $C_2$-$C_{10}$ alkyl or $C_3$-$C_{10}$ alkenyl; preferably $C_2$-$C_{10}$ alkyl; preferably $C_3$-$C_{10}$ alkyl; preferably $C_4$-$C_{10}$ alkyl; preferably $C_4$-$C_8$ alkyl. Preferably alkyl, alkenyl and aralkyl substituents are unsubstituted. Preferably alkyl and alkenyl groups are linear.

Preferably, the amount of the first marker added to the petroleum hydrocarbon or a liquid biologically derived fuel is larger than the amount of the second marker, preferably at least ten times as large, preferably at least 20 times, preferably at least 50 times. Preferably the amount of the second marker is no greater than 50 ppm, preferably no greater than 20 ppm, preferably no greater than 15 ppm, preferably no greater than 10 ppm, preferably no greater than 7 ppm, preferably no greater than 5 ppm, preferably no greater than 3 ppm; preferably at least 0.02 ppm, preferably at least 0.05 ppm, preferably at least 0.1 ppm. Preferably, the amount of the first marker is at least 0.2 ppm, preferably at least 0.5 ppm, preferably at least 1 ppm, preferably at least 2 ppm, preferably at least 3 ppm, preferably at least 5 ppm; preferably no greater than 100 ppm, preferably no greater than 70 ppm, preferably no greater than 50 ppm, preferably no greater than 30 ppm. Preferably, a marker compound is not detectable by visual means in the marked petroleum hydrocarbon or liquid biologically derived fuel, i.e., it is not possible to determine by unaided visual observation of color or other characteristics that it contains a marker compound. Preferably, a marker compound is one that does not occur normally in the petroleum hydrocarbon or liquid biologically derived fuel to which it is added, either as a constituent of the petroleum hydrocarbon or liquid biologically derived fuel itself, or as an additive used therein.

Preferably, the marker compounds have a log P value of at least 3, where P is the 1-octanol/water partition coefficient. Preferably, the marker compounds have a log P of at least 4, preferably at least 5. Log P values which have not been experimentally determined and reported in the literature can be estimated using the method disclosed in Meylan, W. M & Howard, P. H., *J. Pharm. Sci.*, vol. 84, pp. 83-92 (1995). Preferably the petroleum hydrocarbon or liquid biologically derived fuel is a petroleum hydrocarbon, biodiesel fuel or ethanol fuel; preferably a petroleum hydrocarbon or biodiesel fuel; preferably a petroleum hydrocarbon; preferably crude oil, gasoline, diesel fuel, kerosene, jet fuel or heating oil; preferably gasoline or diesel fuel; preferably diesel fuel.

More than one first marker and/or more than one second marker may be present in the fuel. Use of multiple marker compounds facilitates incorporation into the petroleum hydrocarbon or liquid biologically derived fuel of coded information that may be used to identify the origin and other characteristics of the petroleum hydrocarbon or liquid biologically derived fuel. The code comprises the identities and relative amounts, e.g., fixed integer ratios, of the marker compounds. One, two, three or more marker compounds may be used to form the code. Marker compounds according to this invention may be combined with markers of other types, e.g., markers detected by absorption spectrometry, including those disclosed in U.S. Pat. No. 6,811,575; U.S. Pat. App. Pub. No. 2004/0250469 and EP App. Pub. No. 1,479,749. Marker compounds are placed in the petroleum hydrocarbon or liquid biologically derived fuel directly, or alternatively, placed in an additives package containing other compounds, e.g., antiwear additives for lubricants, detergents for gasoline, etc., and the additives package is added to the petroleum hydrocarbon or liquid biologically derived fuel. Use of more than one marker may be useful to avoid removal of a marker by distillation. Preferably, at least two markers are used which differ in boiling point by at least 50° C., preferably at least 75° C., preferably at least 100° C., preferably at least 125° C.

The marker compounds may be prepared by methods known in the art, e.g., allowing an aryloxide salt to react with an alkyl halide to form an aryl alkyl ether.

EXAMPLES

Analytical Conditions:
Automated Liquid Samplers for channel 1 and 2:
Injection size: 2 µL Solvent 1 wash: 3×10 µL Solvent 2 wash: 3×10 µL
Sample rinse: 3×10 µL
Sample pump: 3×10 µL
Air gap: 0.2 µL
Channel 1: (Distillable Marker)
Inlet: Split/Splitless in split mode, split ratio: 20:1, septum purge: 3 mL/min helium
Inlet temperature: 300° C.
Column 1: 15 m×0.25 mm id×0.1 µm, stationary phase: 100% polydimethylsiloxane (DB-1HT); flow: 1 mL/min Helium
Column 2: 23.5 m×0.25 mm id×1 µm, stationary phase: polyethylene glycol 20,000 (VF-WAXms); flow: 1 mL/min Helium
Both Columns in Constant Flow Mode
Oven temperature: 100 C (0.5 min) @10 C/min to 270 C (10 min)
Channel 2: (Non-Distillable Marker)
Inlet: Split/Splitless in split mode, split ratio: 20:1, septum purge: 3 mL/min
Inlet temperature: 300° C.
Column 3: 15 m×0.25 mm-id×0.15 µm; stationary phase: 50% phenyl-substituted polydimethylsiloxane (DB-17HT); flow: 1 mL/min Helium
Column 4: 2.7 m×0.15 mm-id uncoated but deactivated fused silica column connected to MSD; flow: 2 mL/min Helium
Column 5: 2.0 m×0.15 mm-id uncoated but deactivated fused silica column, connected to FID; flow: 2 mL/min Helium
All columns in Constant Flow Mode
Oven temperature: 100 C (0.5 min) @10 C/min to 360° C. (10 min)
Flame Ionization Detector Conditions:
Detector temperature: 350° C.
Hydrogen: 30 mL/min
Nitrogen: 25 mL/min
Air: 350 mL/min
Mass Spectrometer Conditions:
Transfer line temperature: 300° C.
Ion source temperature: 325° C.
Quadrupole temperature: 250° C.
Mode of operation: Selective Ion Monitoring (SIM)
Dwell time 200 ms The First Marker was n-butyl phenyl ether at concentrations from 25 ppb to 5 ppm in commercial diesel fuel (ESSO Canada). It eluted from the First Channel after 8.37 minutes under conditions used. The Second Marker in some runs was 6,6'-((4-trityl-1,2-phenylene)bis(oxy))bis(hexan-1-ol) at concentrations from 50 ppb to 10 ppm. It eluted from the Second Channel after 20.7 minutes. In other runs, the Second Marker was 10,10'-((4-trityl-1,2-phenylene)bis(oxy))bis(decan-1-ol) at concentrations from 50 ppb to 10 ppm, and it eluted from the Second Channel after 24.4 minutes.

The invention claimed is:

1. A gas chromatographic method for detecting a first marker compound and a second marker compound in a petroleum hydrocarbon or a liquid biologically derived fuel; said method comprising providing two analysis channels, (i) and (ii); wherein channel (i) comprises a first capillary column which is an open tubular column coated with a polysiloxane stationary phase and a second capillary column which is an open tubular column coated with a polyethylene glycol; and channel (ii) comprises a third capillary column which is an open tubular column coated with a polymethylphenylsiloxane having at least 30 mole % phenyl substitution and a fourth capillary column which is a deactivated open tubular column; and said method comprising steps of: (a) determining retention times of the first marker compound in the first and second capillary columns and the second marker compound in the third and fourth capillary columns; (b) introducing a first sample of a petroleum hydrocarbon or a liquid biologically derived fuel into the first channel and allowing the first sample to flow through the first capillary column to produce a first effluent stream; (c) introducing only a portion of the first effluent stream having a retention time range which includes the retention time of the first marker compound into the second capillary column and allowing said portion of the first effluent stream to flow through the second capillary column to produce a second effluent stream; (d) allowing the second effluent stream to pass through a mass spectrometer; (e) introducing a second sample of a petroleum hydrocarbon or a liquid biologically derived fuel into the second channel and allowing the sample to flow through the third capillary column to produce a third effluent stream; (f) introducing only a portion of the third effluent stream having a retention time range which includes the retention time of the second marker compound into the fourth capillary column and allowing said portion of the third effluent stream to flow through the fourth capillary column to produce a fourth effluent stream; and (g) allowing the fourth effluent stream to pass through a mass spectrometer;

wherein the first marker compound has formula $Ar^1(R^2)_m(OR^1)_n$, wherein $Ar^1$ is an aromatic ring system having from six to twenty carbon atoms, $R^1$ is $C_1$-$C_{12}$ alkyl or $C_2$-$C_{12}$ alkenyl, $R^2$ is $C_1$-$C_{12}$ alkyl or $C_3$-$C_{12}$ alkenyl, m is an integer from zero to five and n is an integer from one to three; the second marker compound has three or four un-fused benzene rings, a total of 20 to 60 carbon atoms and at least one alkyl or alkoxy substituent having one to eighteen carbon atoms; and wherein each marker compound is present in the petroleum hydrocarbon or a liquid biologically derived fuel at a level from 0.01 ppm to 100 ppm.

2. The method of claim 1 in which $Ar^1$ is a benzene ring system and R is $C_4$-$C_{12}$ alkyl.

3. The method of claim 2 in which a portion of the first effluent stream which is not introduced into the second capillary column and a portion of the third effluent stream which is not introduced into the fourth capillary column are diverted using a non-contact switching device.

4. The method of claim 3 in which the second marker compound has 25 to 50 carbon atoms and at least two substituents chosen from the group consisting of alkyl and alkoxy; wherein each substituent has from one to twelve carbon atoms.

5. The method of claim 4 in which the polysiloxane stationary phase is polydimethylsiloxane; the polyethylene glycol has a number average molecular weight from 15,000 to 25,000; and the polymethyphenylsiloxane is a polydimethylsiloxane in which at least 40 mole % of methyl groups has been replaced with phenyl groups.

6. The method of claim 5 in which at least 70 wt % of the third effluent is vented and not transferred to the fourth column.

7. The method of claim 6 in which the second marker compound has formula $(Ph_3C)_k Ar^2(R^3)_j(OR^4)_i$, wherein Ph represents a phenyl group, $Ar^2$ is an aromatic ring system having from six to twenty carbon atoms, $R^3$ and $R^4$ independently are $C_1$-$C_{18}$ alkyl, $C_3$-$C_{18}$ alkenyl or $C_4$-$C_{18}$ heteroalkyl, k is one, j is an integer from one to four and i is an integer from one to three.

* * * * *